(12) United States Patent
Li et al.

(10) Patent No.: US 12,220,411 B1
(45) Date of Patent: Feb. 11, 2025

(54) APPLICATION OF PTGDS INHIBITOR IN PREPARATION OF DRUG FOR TREATING CATARACTS

(71) Applicant: THE EYE HOSPITAL OR WENZHOU MEDICAL UNIVERSITY, Wenzhou (CN)

(72) Inventors: Jin Li, Wenzhou (CN); Jiasheng Liu, Wenzhou (CN); Yitong Xu, Wenzhou (CN); Mengchao Zhu, Wenzhou (CN); Haisen Sun, Wenzhou (CN)

(73) Assignee: THE EYE HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 18/692,452

(22) PCT Filed: Oct. 8, 2023

(86) PCT No.: PCT/CN2023/123329
§ 371 (c)(1),
(2) Date: Mar. 15, 2024

(30) Foreign Application Priority Data

Jul. 25, 2023 (CN) .......................... 202310914152.1

(51) Int. Cl.
*A61K 31/454* (2006.01)
*A61P 27/12* (2006.01)

(52) U.S. Cl.
CPC ............ *A61K 31/454* (2013.01); *A61P 27/12* (2018.01)

(58) Field of Classification Search
CPC ............................... A61K 31/454; A61P 27/12
See application file for complete search history.

(56) References Cited

U.S. PATENT DOCUMENTS

2015/0285800 A1* 10/2015 Ragolia ................ A61K 31/137
514/390
2016/0228584 A1 8/2016 Lin et al.

FOREIGN PATENT DOCUMENTS

| CN | 101039920 A | 9/2007 |
| CN | 101146770 A | 3/2008 |
| CN | 101495449 A | 7/2009 |
| JP | H04-253909 A | 9/1992 |
| WO | WO 95/01350 A1 | 1/1995 |

OTHER PUBLICATIONS

Irikura, Daisuke, et al., "Biochemical, Functional, and Pharmacological Characterization of AT-56, an Orally Active and Selective Inhibitor of Lipocalin-type Prostaglandin D Synthase," *The Journal of Biological Chemistry*, vol. 284, No. 12, pp. 7623-7630 (Mar. 20, 2009).

Bauer, MD, Gregor, et al., "Lipocalin-like Prostaglandin D Synthase (L-PGDS) Concentration in Aqueous Humour in Patients With Open-angle Glaucoma," *J Glaucoma*, vol. 23, No. 3, pp. 164-168 (Mar. 2014).

Gao, Jie, et al., "Research progress on the application of non steroidal anti-inflammatory drugs in cataract surgery," *International Eye Science*, vol. 10, Issue 11, pp. 2133-2136 (Nov. 3, 2010).

Dong, Dongsheng, et al., "Study on the biosynthesis of prostaglandins in the lens of galactose induced cataracts in rats," *Eye*, vol. 7, Issue 3, pp. 187-189 (Aug. 31, 1998).

Gao, Yuan, et al., "The relationship between cyclooxygenase-2 and eye diseases," *Foreign medicine, Ophthalmology*, vol. 29, Issue 4, pp. 245-248 (Aug. 31, 2005).

* cited by examiner

*Primary Examiner* — Timothy R Rozof
(74) *Attorney, Agent, or Firm* — Christensen, Fonder, Dardi & Herbert PLLC

(57) ABSTRACT

Application of a PTGDS inhibitor in preparation of a drug for treating cataracts is provided. As an effective and selective PTGDS inhibitor, AT-56 competitively inhibits production of PGD2 by occupying a catalytic site of PTGDS. The PTGDS catalyzes synthesis of the PGD2 to cause an oxidative stress injury of human lens epithelial cells, thereby promoting occurrence and development of aging and opacity of a lens. By reducing apoptosis caused by the oxidative stress injury, a degree of the cataracts can be effectively reduced.

2 Claims, 23 Drawing Sheets
(17 of 23 Drawing Sheet(s) Filed in Color)

A:0 Cluster GSEA of arachidonic acid metabolism pathway

B:1 Cluster GSEA of arachidonic acid metabolism pathway

C:2 Cluster GSEA of arachidonic acid metabolism pathway

D:3 Cluster GSEA of arachidonic acid metabolism pathway

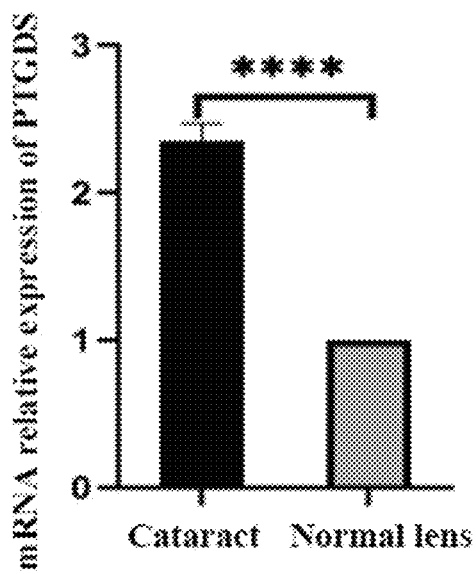
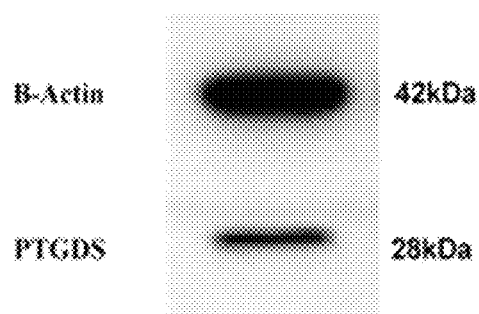
FIG. 6A
FIG. 6B
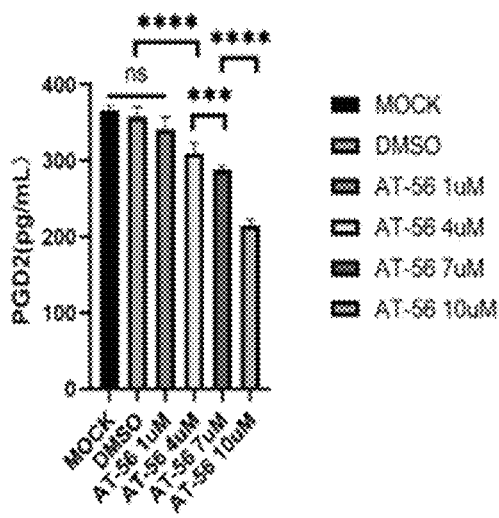
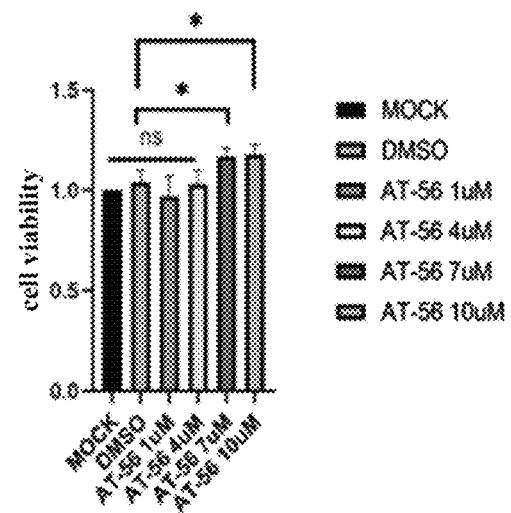
FIG. 6C
FIG. 6D

A

B

C

D

APPLICATION OF PTGDS INHIBITOR IN PREPARATION OF DRUG FOR TREATING CATARACTS

RELATED APPLICATIONS

The present application is a National Phase entry of PCT Application No. PCT/CN2023/123329, filed Oct. 8, 2023, which claims priority to Chinese Patent Application No. 202310914152.1, filed Jul. 25, 2023, the disclosures of which are hereby incorporated by reference herein in their entirety.

TECHNICAL FIELD

The present invention relates to the technical field of cataract treatment, and in particular to an application of a PTGDS inhibitor in the preparation of a drug for treating cataracts.

BACKGROUND

Cataracts are partial or whole opacity of lenses, which results in progressive loss of vision. The cataracts are the main cause of blindness. According to statistics, the cataracts account for one-third of all causes of the blindness in China. At the same time, they are also the second major cause of severe visual impairments and moderate visual impairments after uncorrected refractive errors. Among all types of cataracts, age-related cataracts take up the highest proportion. Some large-scale research reports based on populations have shown that a prevalence rate of age-related cataracts is increased with the increase of age, from 3.9% at 55-64 years old to 92.6% at over 80 years old. With society's population growth and increased aging population, there will be more patients with cataracts, which causes a greater burden to individuals and to society. At present, the most effective method for treating age-related cataracts is surgical treatment, but there is the possibility of intraoperative and postoperative complications such as posterior capsule ruptures, posterior cataracts, and corneal endothelial decompensation. Therefore, a molecular mechanism of aging and opacity of a lens may be understood to provide a potential target for drug treatment for age-related cataracts. Embodiments of the present disclosure alleviate and delay occurrence and development of cataracts.

The lens is composed of lens epithelial cells (LECs) and fibroblasts, and the lens epithelial cells are closely attached to an inner surface of an anterior lens capsule. During growth of the lens, after proliferating in a germinal zone of the lens, the lens epithelial cells are differentiated into lens fibroblasts at an equator of the lens. The lens epithelial cells are the most active sites of metabolism in the lens. They play an important role in growth, differentiation and an injury repair of the lens, and in protecting the transparency and the internal environment stability of the entire lens.

A single-cell transcriptome sequencing technology is a new revolutionary technology that has emerged in recent years. Compared with traditional bulk transcriptome sequencing, the single-cell transcriptome sequencing technology can perform an unbiased, repeatable, high-resolution and high-throughput transcriptome analysis on single cells, which can draw a gene expression profile of the single cells. It reveals a regulatory relationship between a complex and rare cell population and genes. The technology determines a disease-related cell population in a comprehensive and unbiased way and can find the effects of the genes on diseases at a cellular level, so that it can be widely applied to disease researches. It is undeniable that the single-cell transcriptome sequencing technology provides an unprecedented opportunity to find targets for treating the diseases.

However, there is no related research on application of the single-cell transcriptome sequencing technology to exploring the molecular mechanism related to aging and opacity of the lens in current literatures. Therefore, embodiments of the present disclosure perform single-cell transcriptome sequencing on the epithelial cells of an aged opaque lens and a transparent lens, acquire significant differential genes and a related pathway between two samples through bioinformatics analysis, and apply an in vitro culture model for the lens epithelial cells and rat in vitro lens organ culture to related verification.

So far, a lanosterol drug has shown a certain clinical effect on drug treatment for the cataracts. Through research on the drug for two congenital cataract families, it is found that lanosterol in a normal lens is the key to regulating abnormal aggregation and depolymerization of lens proteins, which is a great breakthrough in drug treatment for the cataracts. However, as the data does not integrate age-related cataract data, a current clinical experiment also shows some deficiencies, for example, the drug has no significant effect on age-related nuclear cataracts.

SUMMARY OF THE INVENTION

In order to solve the technical defects of a shortage in existing drug treatment for cataracts, the present invention provides application of a prostaglandin D synthase (PTGDS) inhibitor in the preparation of a drug for treating cataracts, capable of delaying and reversing occurrence and development of the cataracts.

Technical solutions employed by the present invention are as follows: Application of a PTGDS inhibitor in the preparation of a drug for treating cataracts is provided, wherein the PTGDS inhibitor is 4-dibenzo[a,d]cyclohepten-5-ylidene-1-[4-(2H-tetrazol-5-yl)-butyl]-piperidine (AT-56).

A concentration of AT-56 as the PTGDS inhibitor in the drug for treating the cataract is 7-10 μM.

The drug for treating the cataracts is a drug for treating age-related cataracts.

Application of a PTGDS inhibitor being AT-56 in the preparation of a drug for treating an oxidative stress injury of lens epithelial cells is provided.

A concentration of the AT-56 as the PTGDS inhibitor in the drug for treating the oxidative stress injury of the lens epithelial cells is 10 μM.

The present invention has the beneficial effects that the present invention provides the application of the PTGDS inhibitor in the preparation of the drug for treating the cataracts. As an effective and selective PTGDS inhibitor, AT-56 competitively inhibits production of PGD2 by occupying a catalytic site of PTGDS. The PTGDS catalyzes synthesis of the PGD2 to cause an oxidative stress injury of human lens epithelial cells, thereby promoting occurrence and development of aging and opacity of a lens. By reducing apoptosis caused by the oxidative stress injury, a degree of the cataracts can be effectively reduced.

BRIEF DESCRIPTION OF THE DRAWINGS

The patent or patent application file contains at least one drawing executed in color. Copies of this patent or patent application publication with color drawing(s) will be provided by the Patent and Trademark Office upon request and payment of the necessary fee.

FIG. 6 is a diagram, in which A shows relative expression of PTGDS between two samples; B shows expression of the PTGDS in a lens epithelial cell line; C shows expressions of the PTGDS at different AT-56 concentrations; and D shows differences in cell activity between various groups with the addition of different concentrations of AT-56;

DETAILED DESCRIPTION OF THE INVENTION

The technical solutions in embodiments of the present invention are clearly and completely described below in combination with the accompanying drawings in the embodiments of the present invention. Apparently, the embodiments described are merely some embodiments rather than all embodiments of the present invention. All other embodiments obtained by those of ordinary skill in the art on the basis of the embodiments of the present invention without making creative efforts fall within the protection scope of the present invention.

In the research of the present invention, it was found that there was a significant difference in a PTGDS (Prostaglandin-H2 D-isomerase) gene and its arachidonic acid metabolism pathway between an aged opaque lens and a transparent lens. PTGDS was purified from a rat brain by Urade Y, et al. in 1985. In an arachidonic acid metabolism signaling pathway, as a prostaglandin H2 (PGH2) D-isomerase, PTGDS could catalyze isomerization of a 9, 11-loop endoperoxide group of PGH2 to produce prostaglandin D2 (PGD2) with a 9-hydroxyl group and a 11-keto group. Arachidonic acid (AA) is the most abundant, active and widely distributed polyunsaturated essential fatty acid in a human body. The arachidonic acid has very strong biological activity, and is closely related to oxidative stress. Among organic inhibitors, as an effective and selective PTGDS inhibitor, AT-56 competitively inhibits production of PGD2 by occupying a catalytic site of PTGDS.

Embodiment 1

Figure 1A:
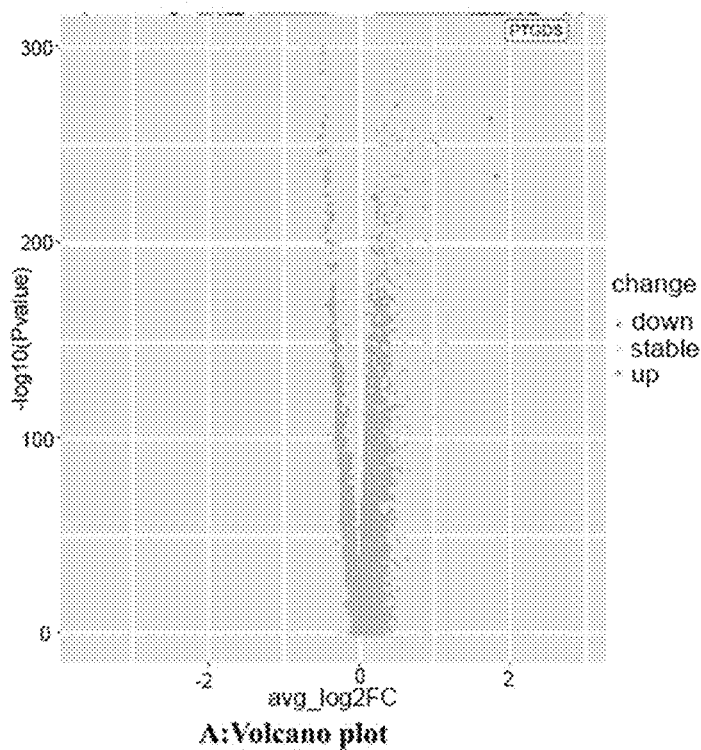
FIG. 1A shows overall results of single-cell transcriptome sequencing.
Figure 1B:
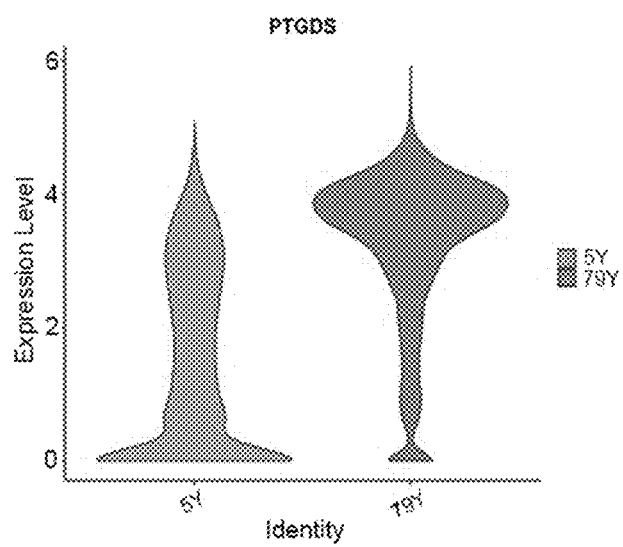
FIG. 1B shows up-regulated and down-regulated gene expressions of PTGDS in a cataract sample compared with a transparent lens sample, as shown in a violin plot.
Figure 1C:
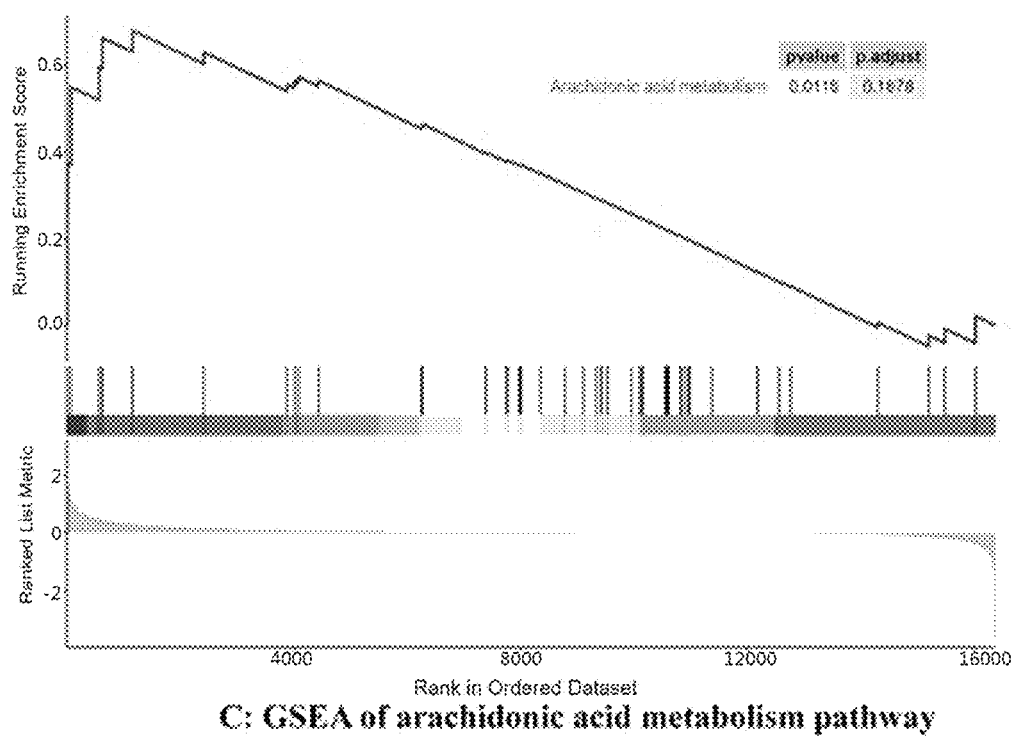
FIG. 1C shows GSEA on 21884 genes through a KEGG database.
Figure 1D:
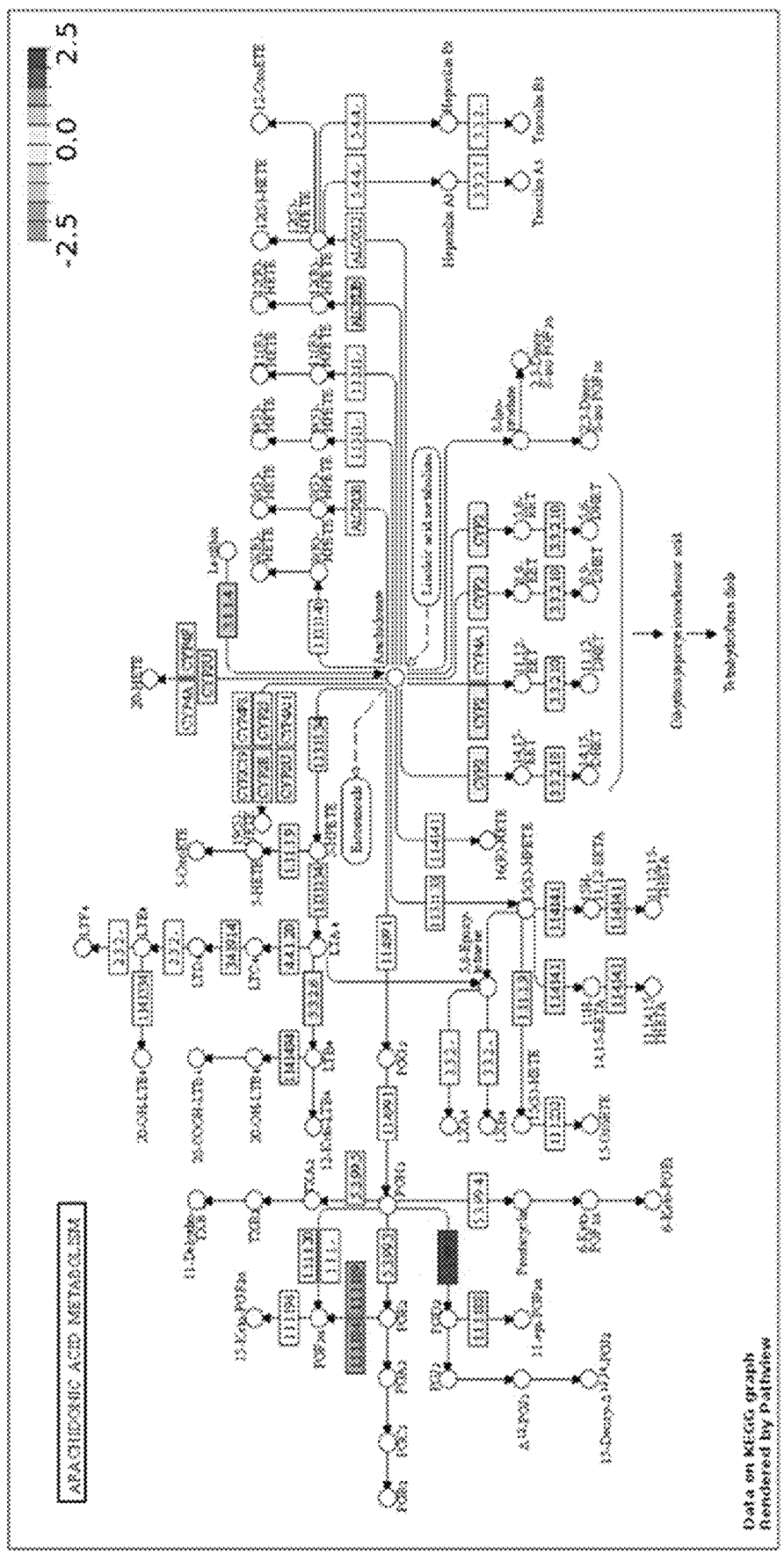
FIG. 1D is a visualization picture of differential genes in an arachidonic acid metabolism signaling pathway.
Figure 2A:
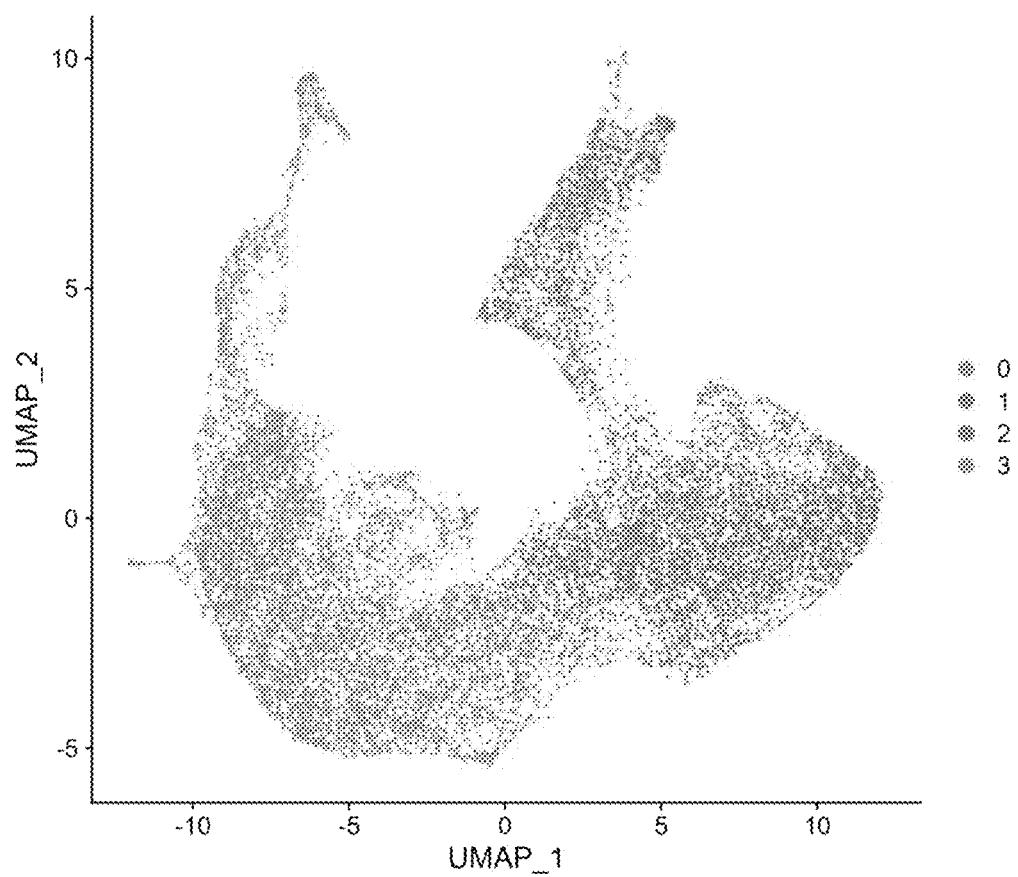
FIG. 2 is a diagram, in which A shows four epithelial cell subgroups of total samples; and in B-E, a number of each subgroup corresponds to top 10 differential genes of 0-3 lens epithelial cell subgroups.
Figure 2B:
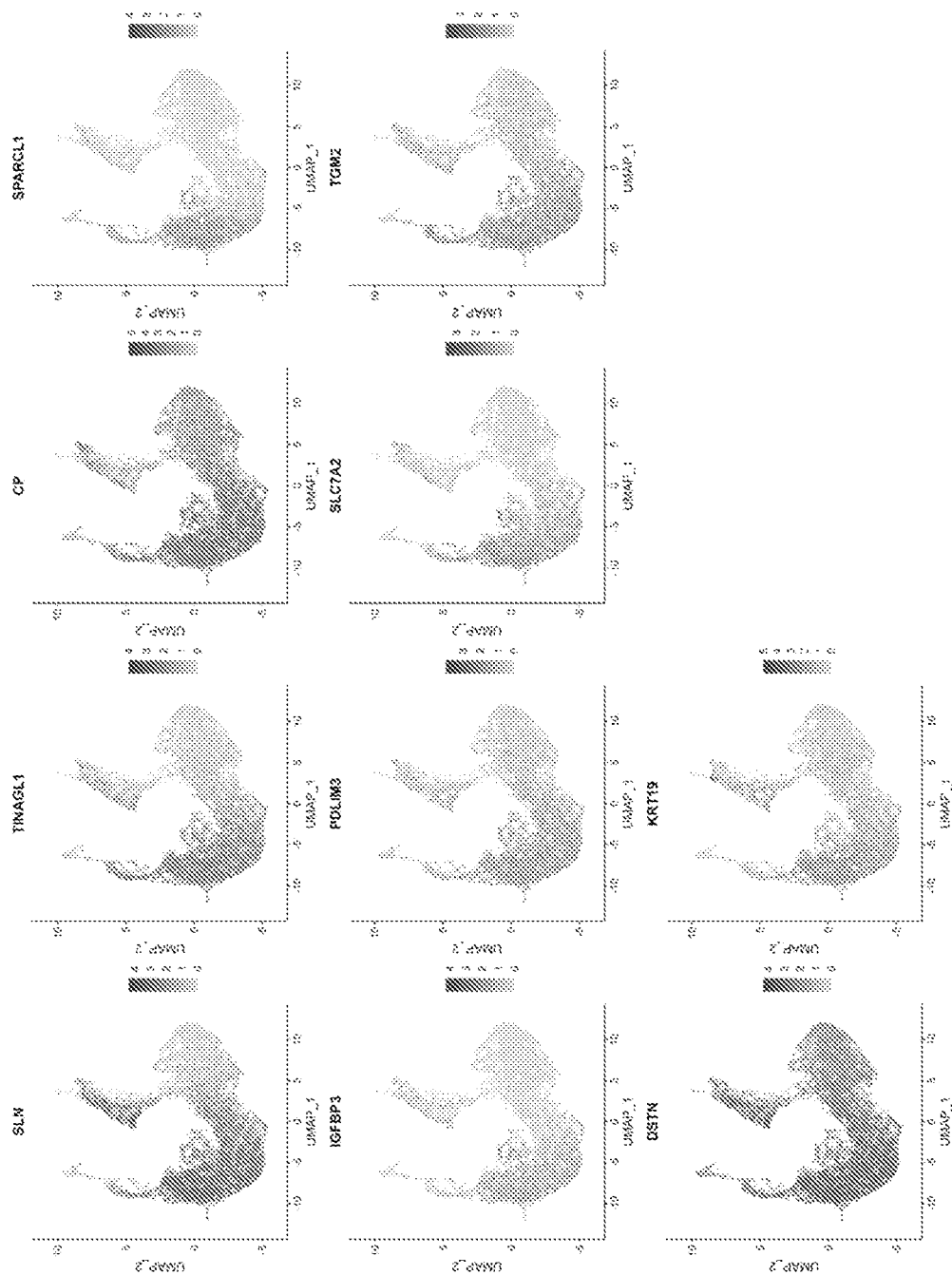
Figure 2C:
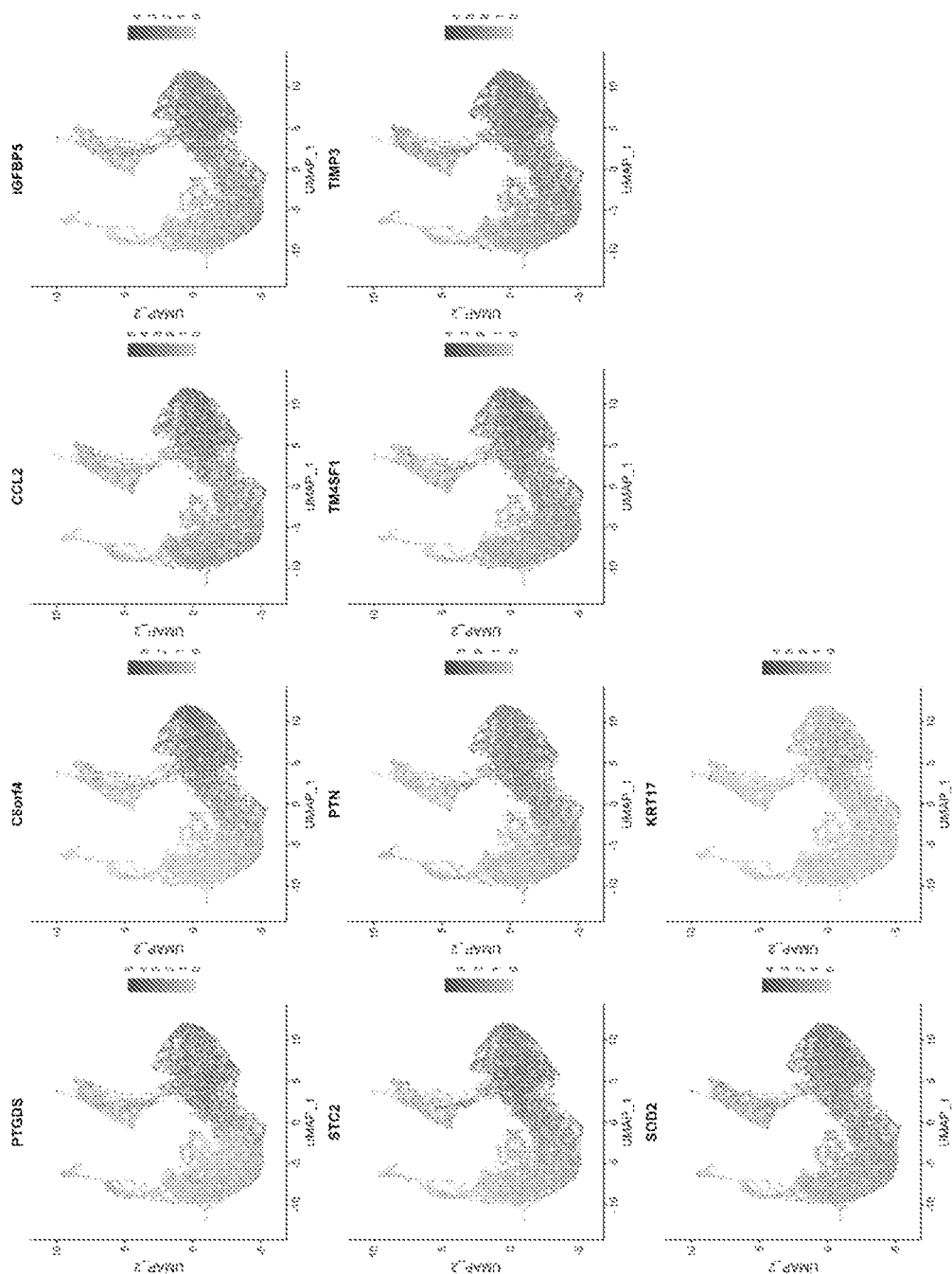
Figure 2D:
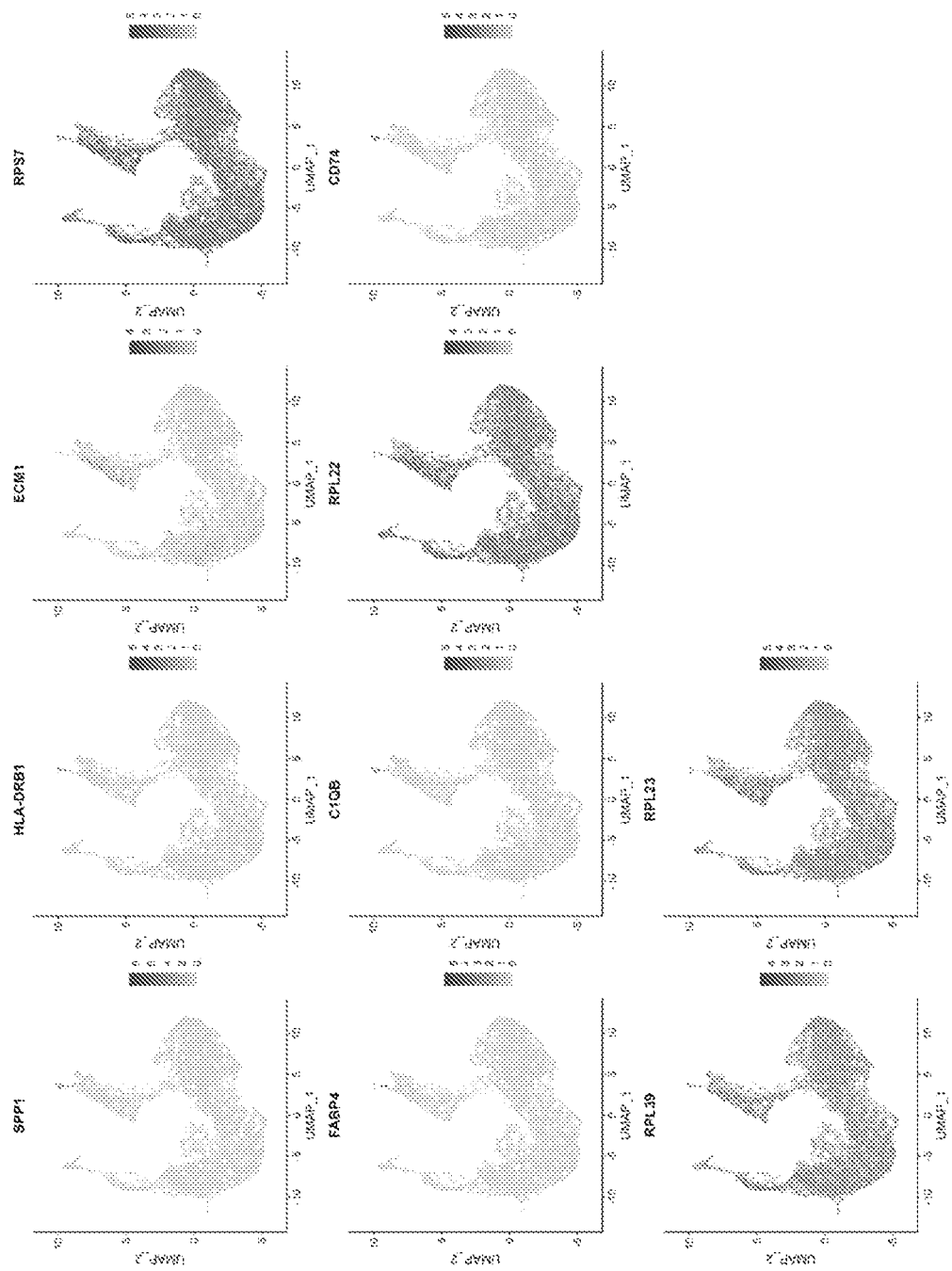
Figure 2E:
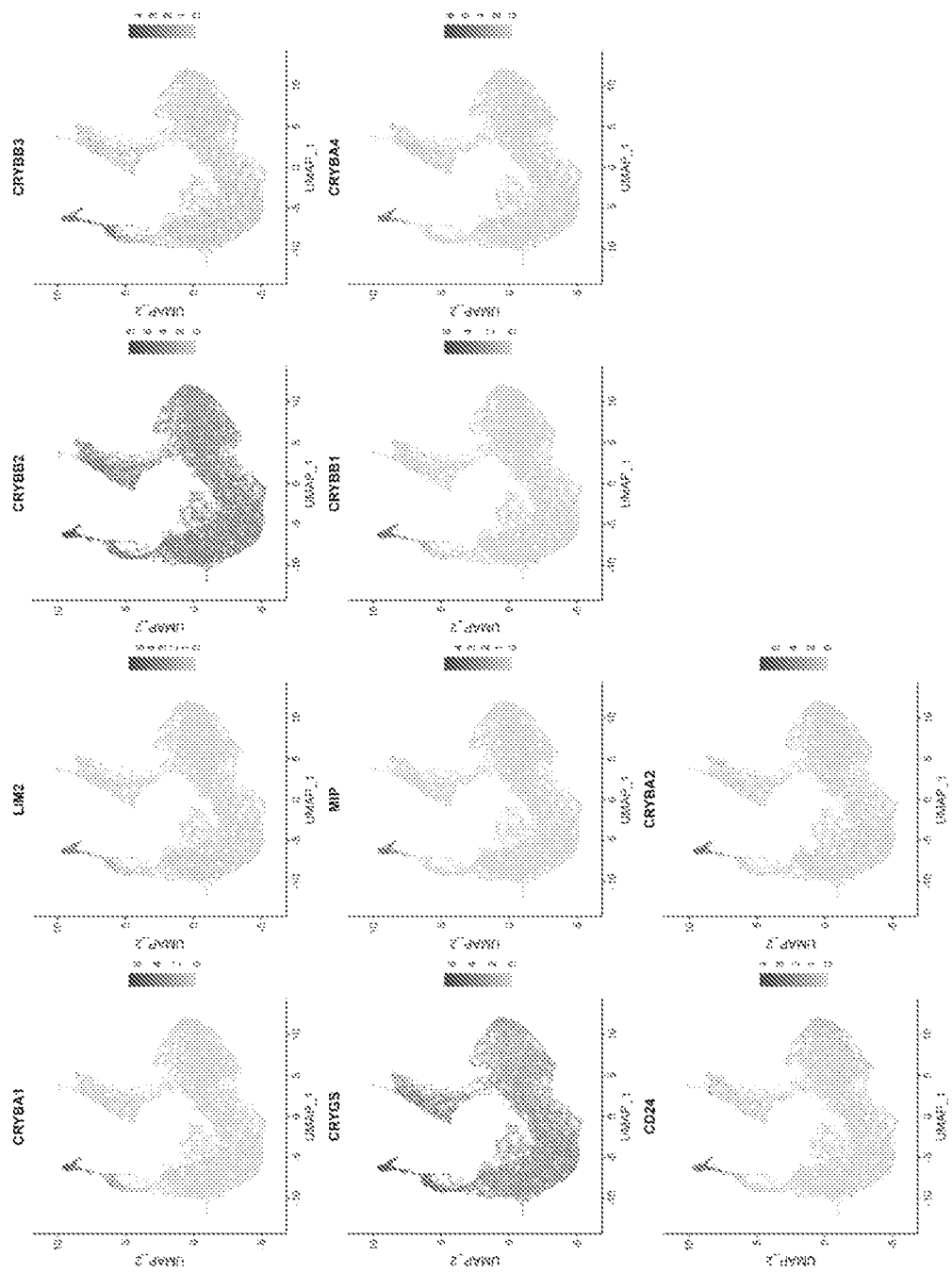
Figure 3A:
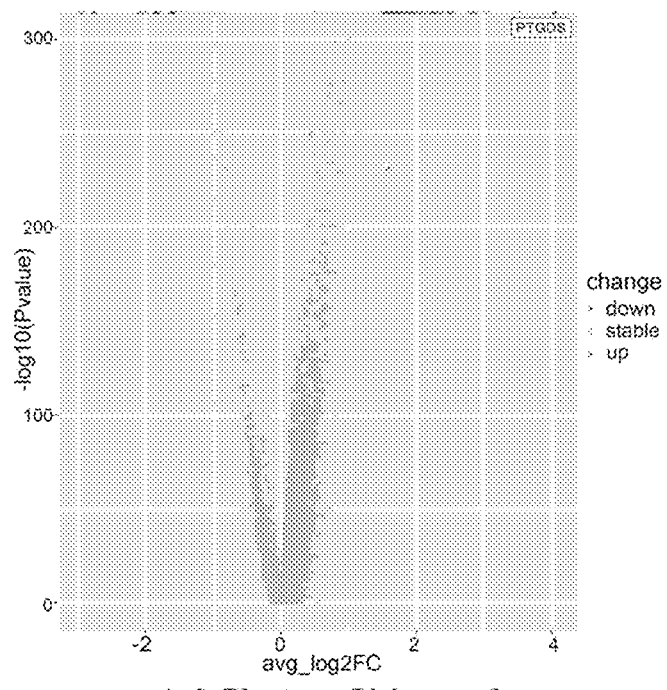
FIG. 3 shows volcano plots (A-D) of differential genes of various subgroups; and E-H show expression levels of PTGDS in various subgroups of two samples.
Figure 3B:
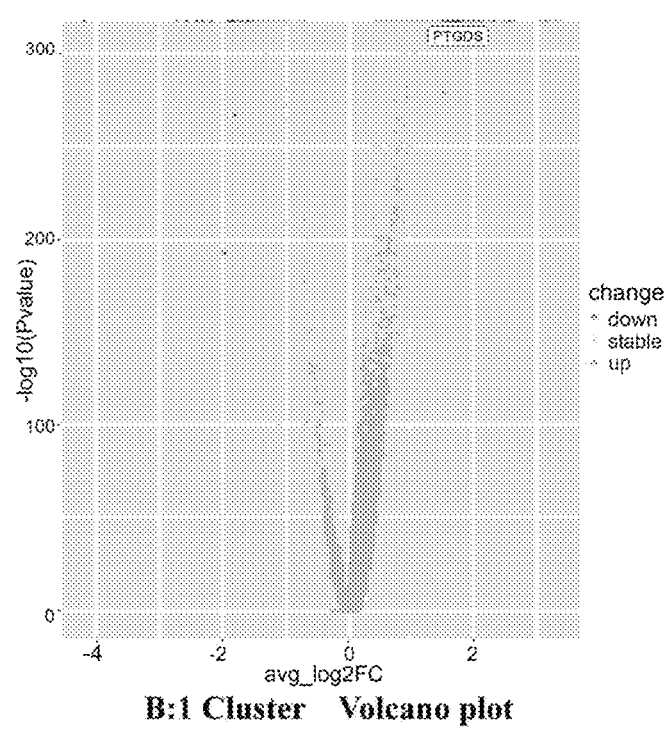
Figure 3C:
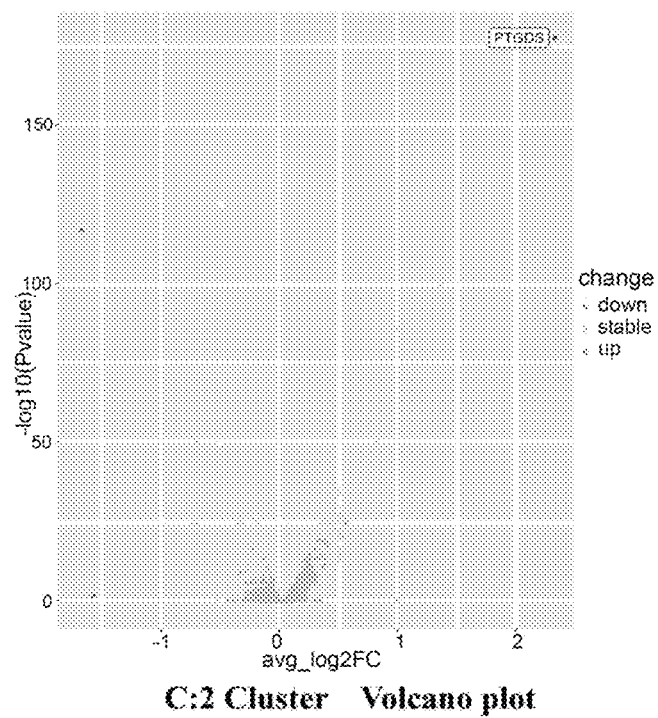
Figure 3D:
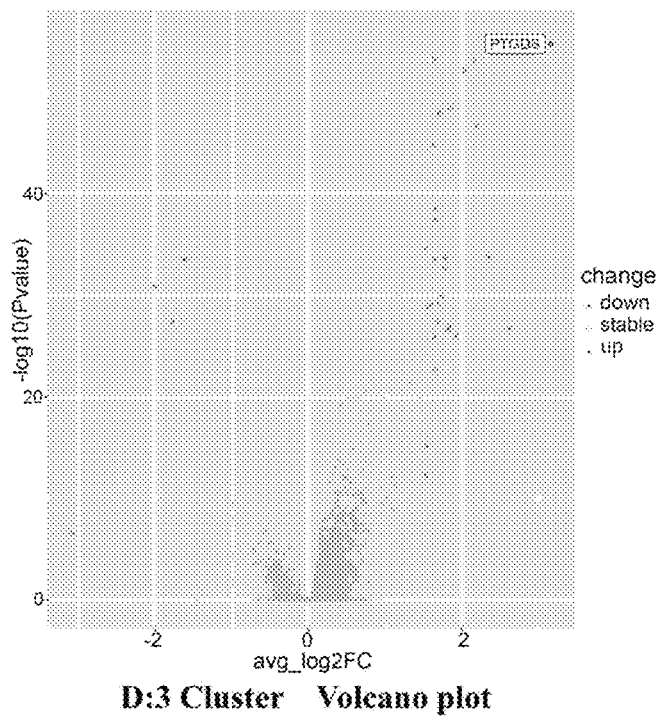
Figure 3E:
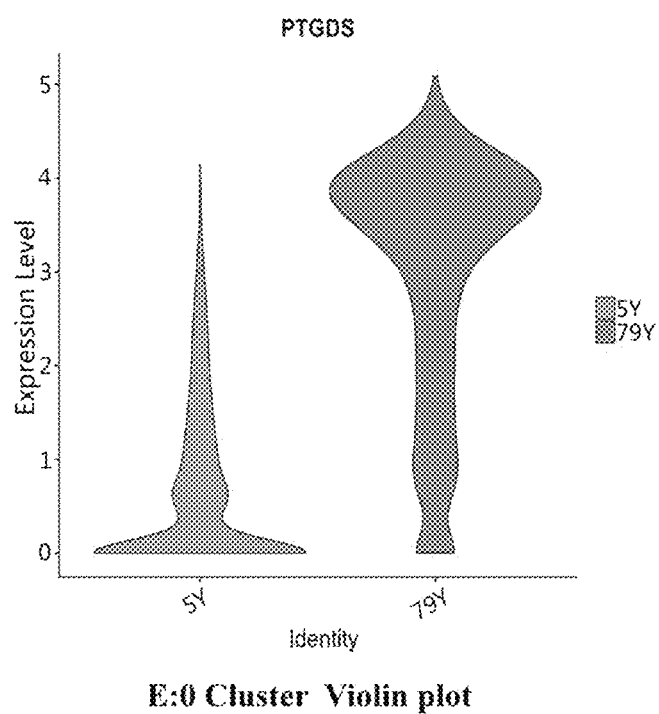
Figure 3F:
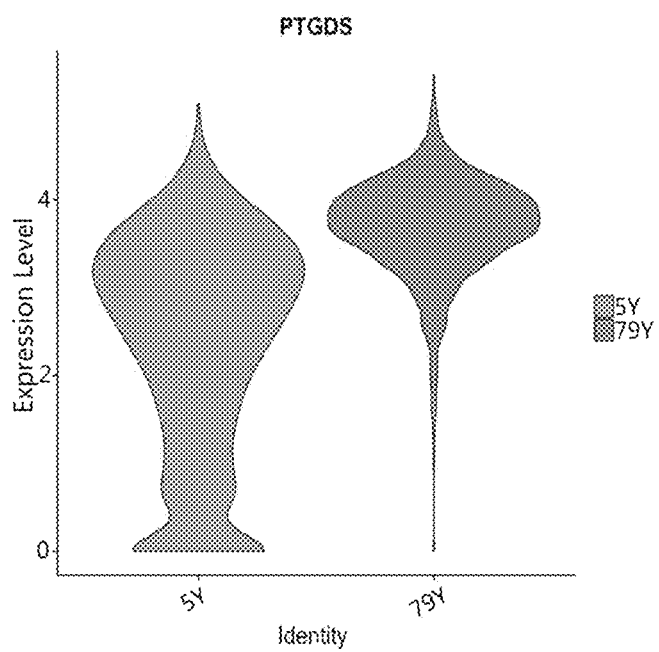
Figure 3G:
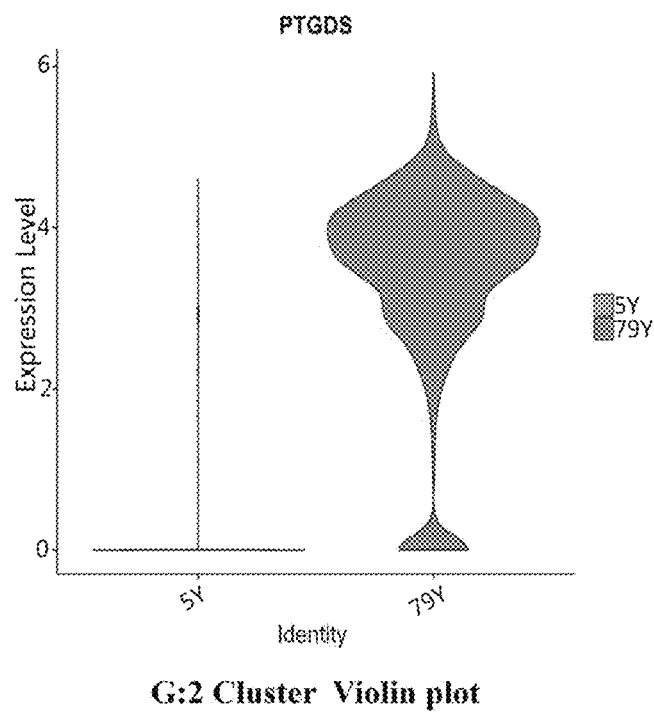
Figure 3H:
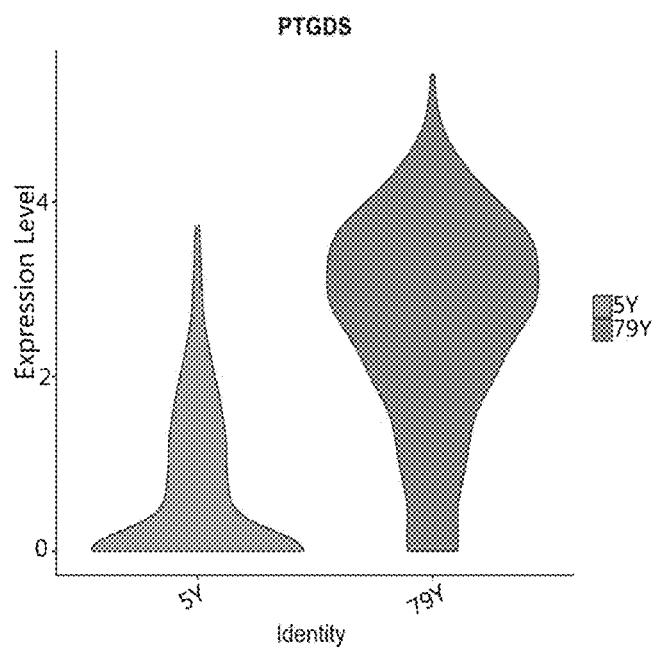
Figure 4A:
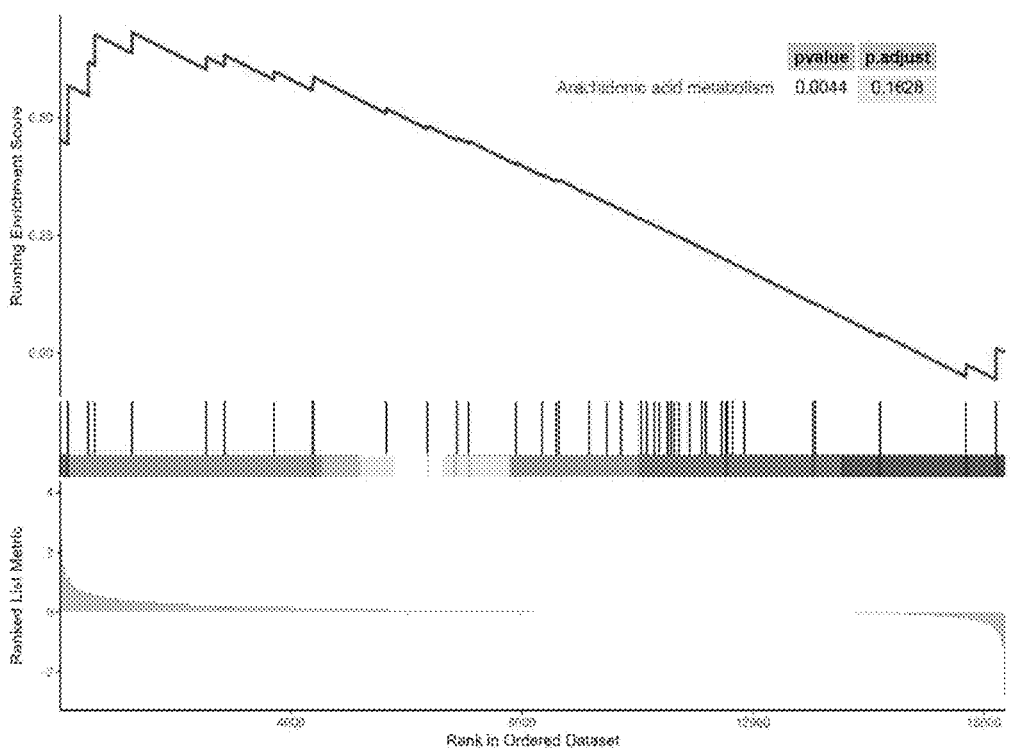
FIG. 4 shows GSEA of arachidonic acid metabolism signaling pathways in various subgroups.
Figure 4B:
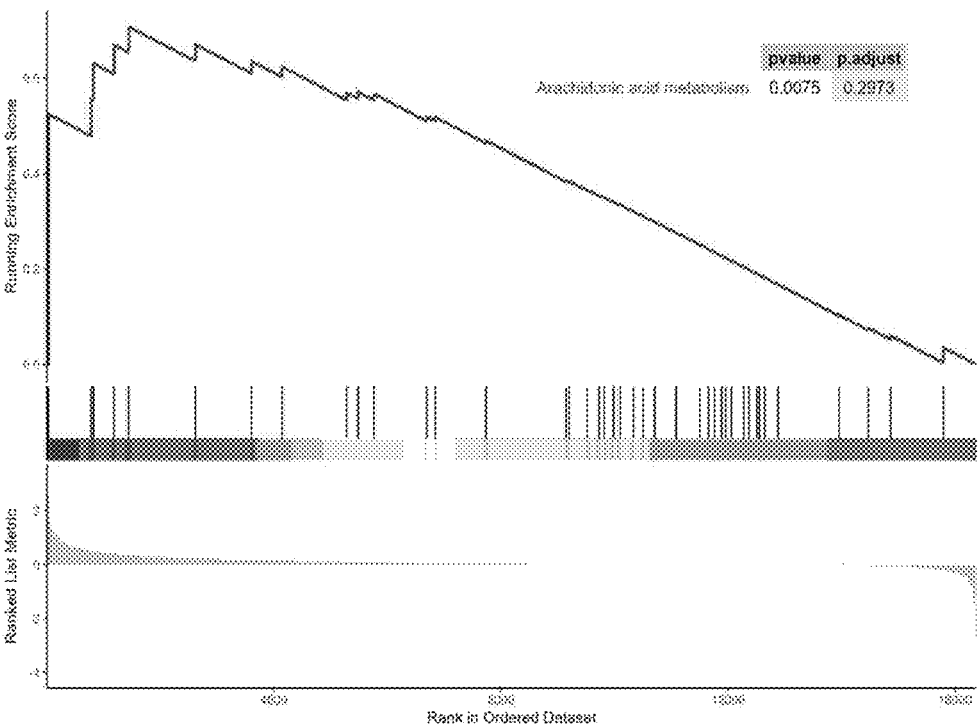
Figure 4C:
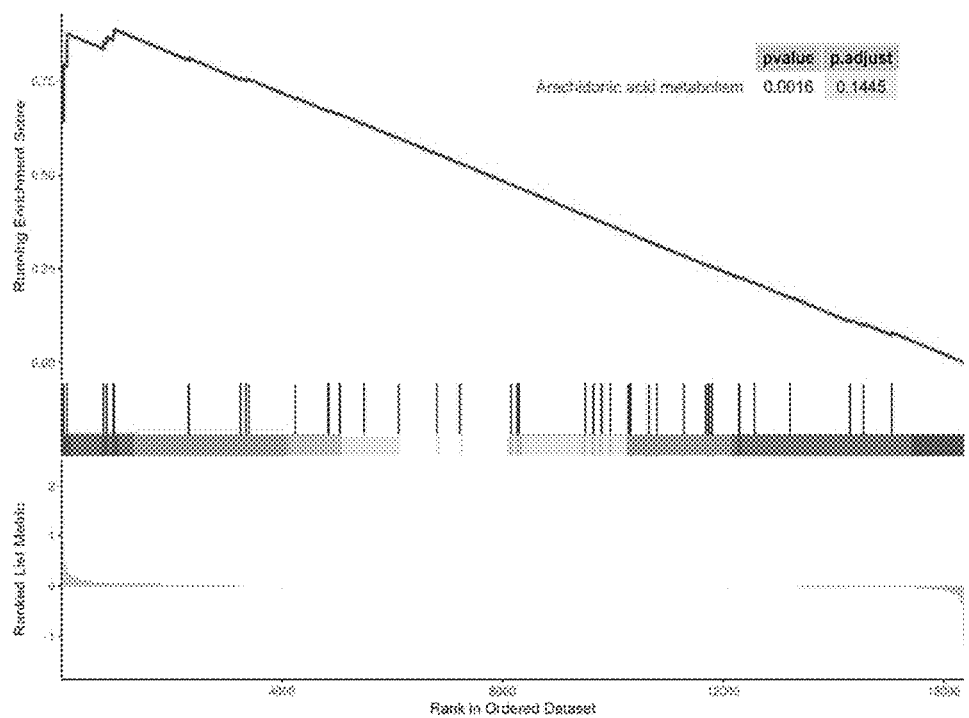
Figure 4D:
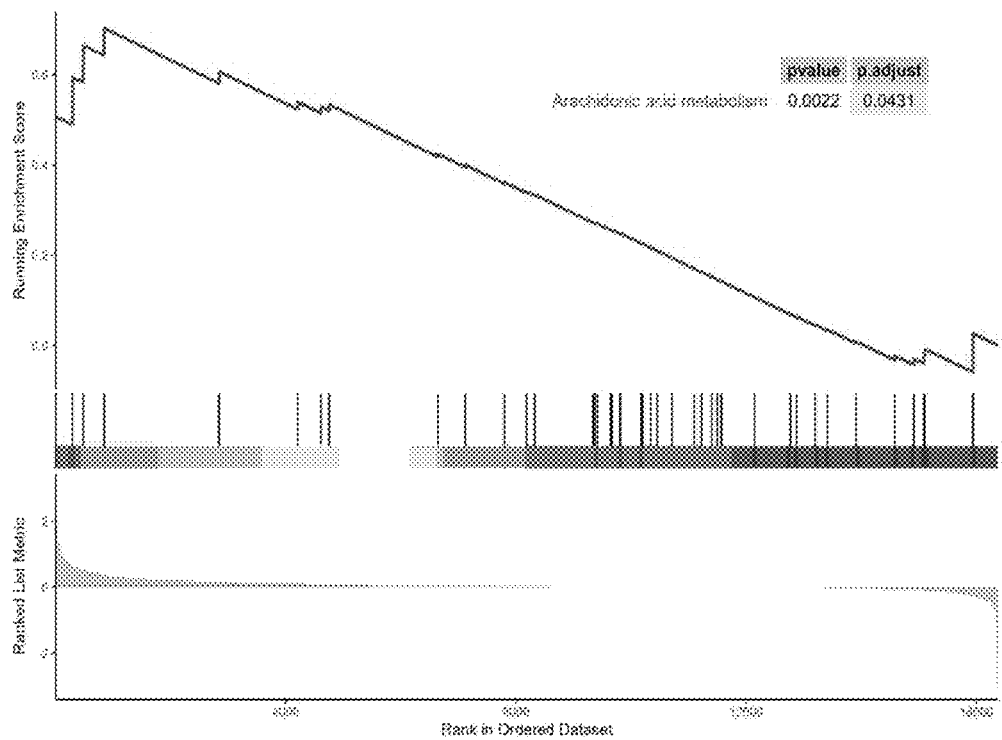
Figure 5A:
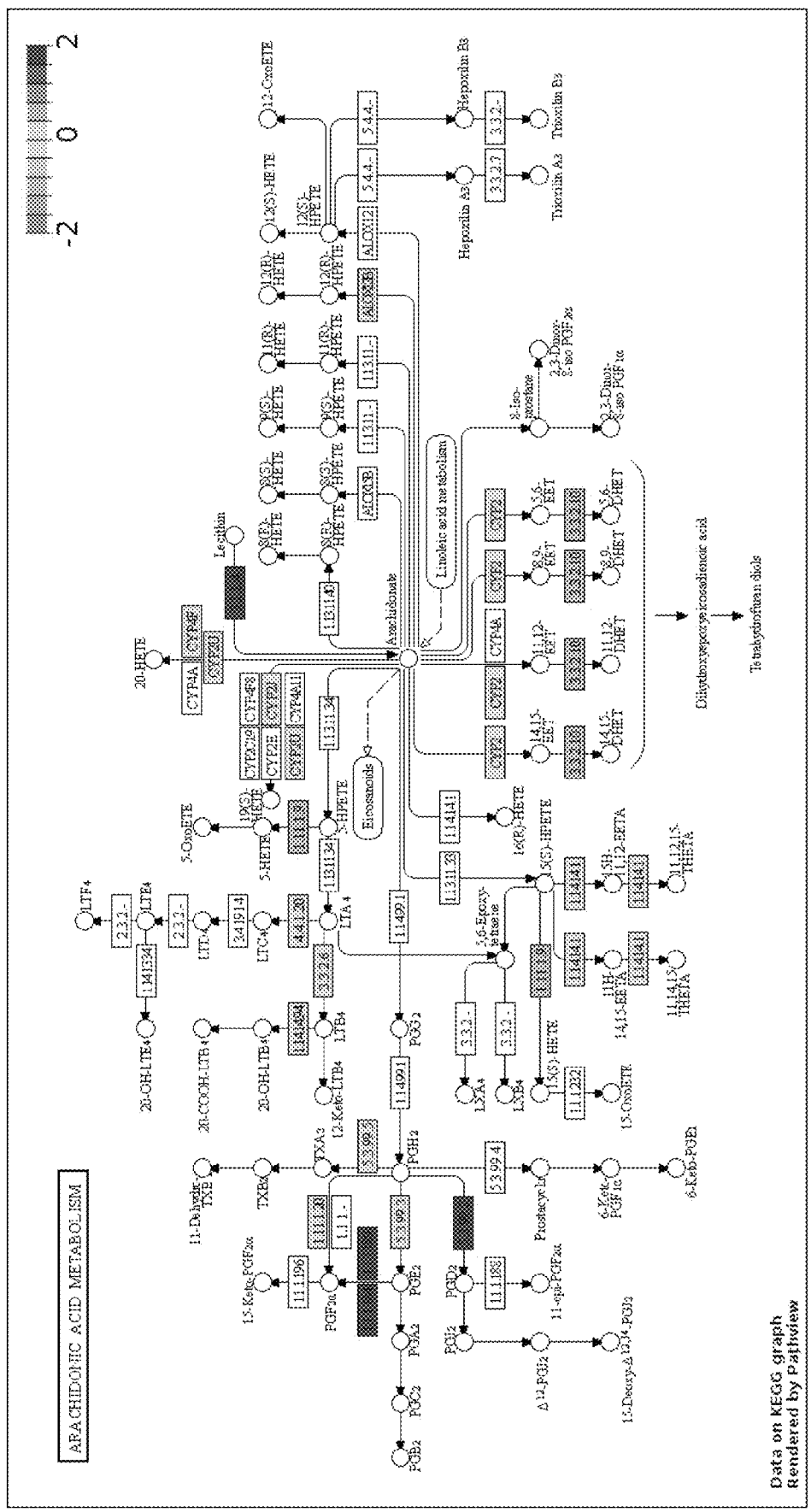
FIG. 5 is a visualization diagram of differential genes of arachidonic acid metabolism signaling pathways in various subgroups.
Figure 5B:
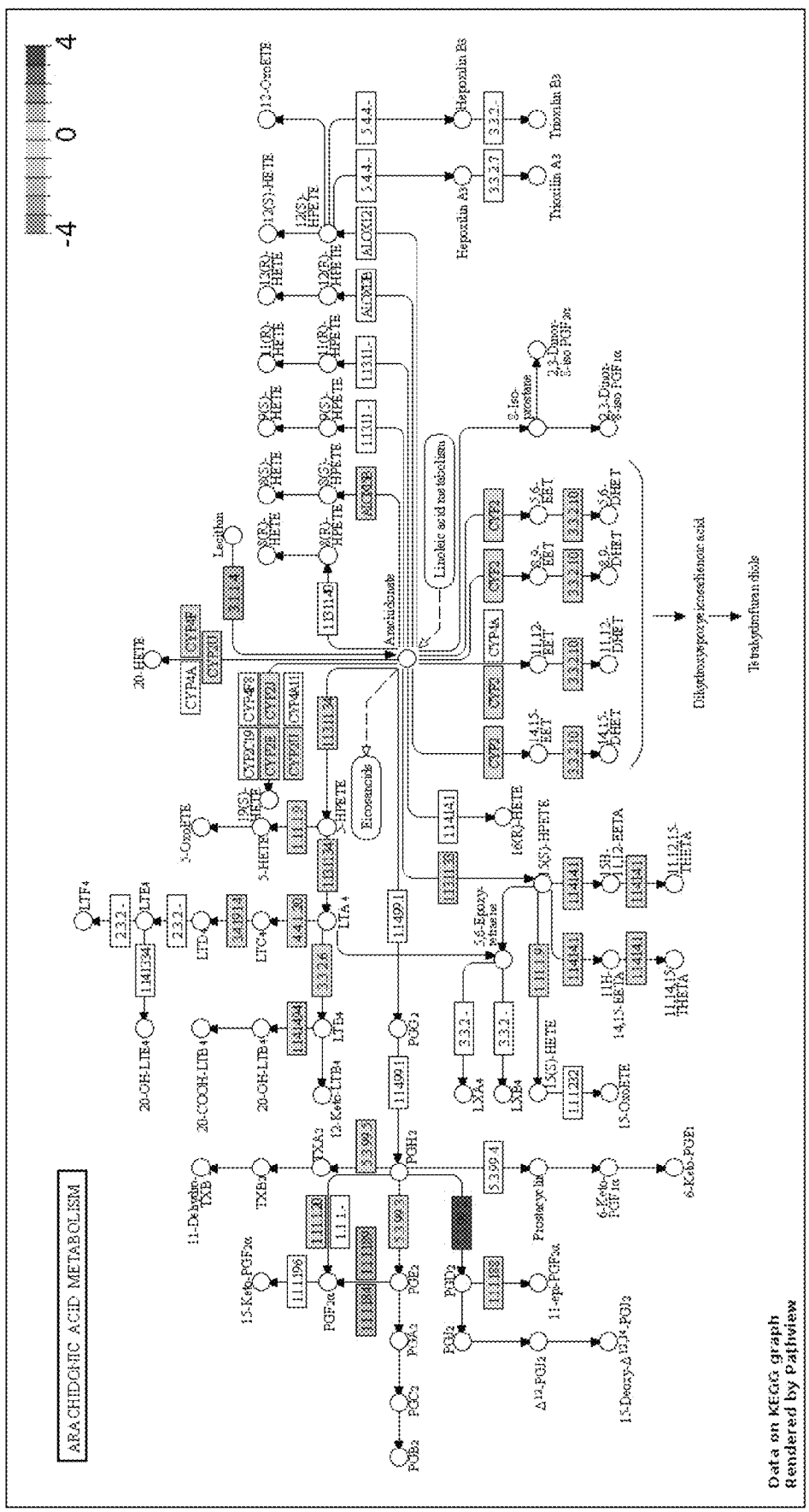
Figure 5C:
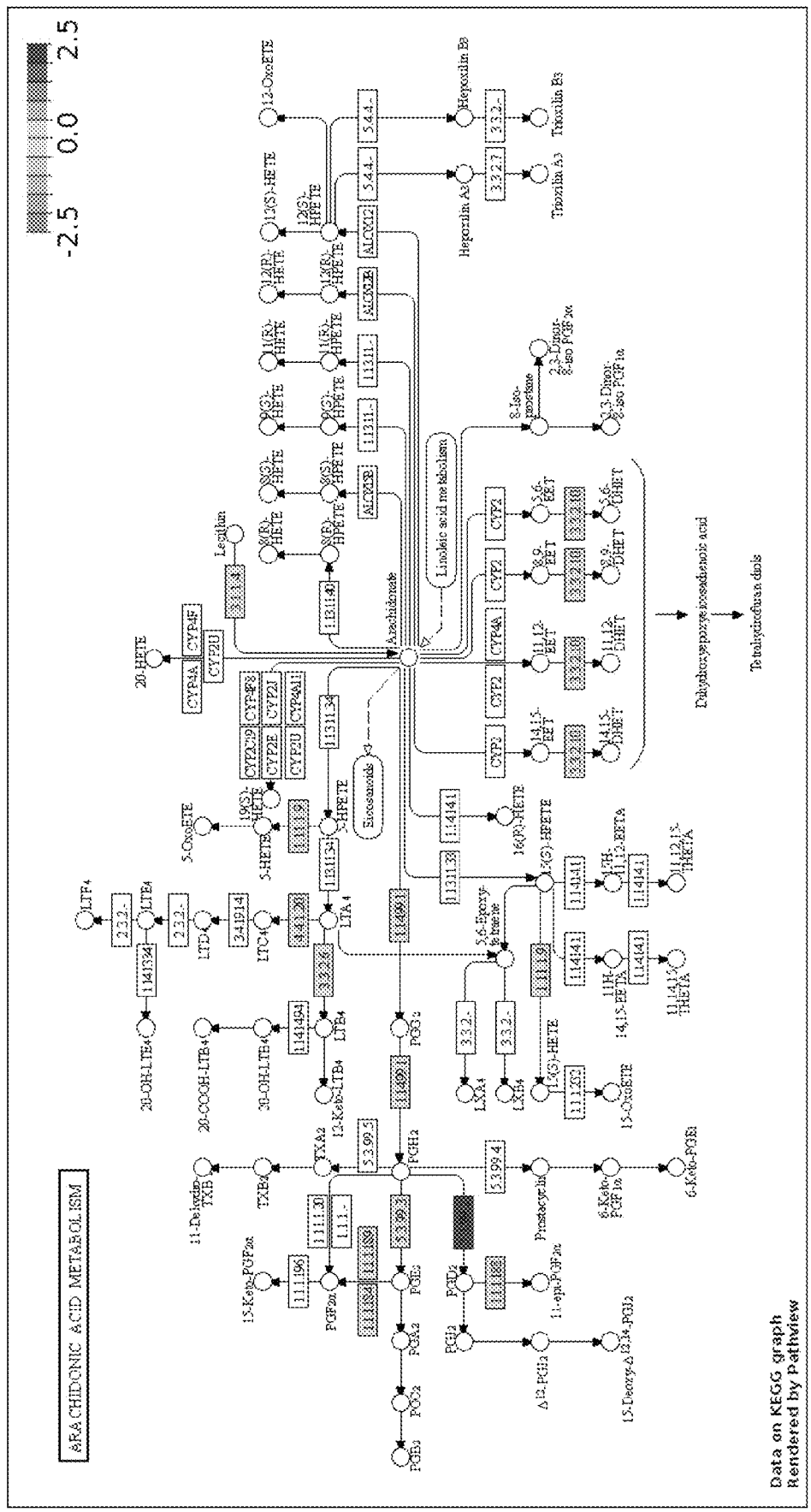
Figure 5D:
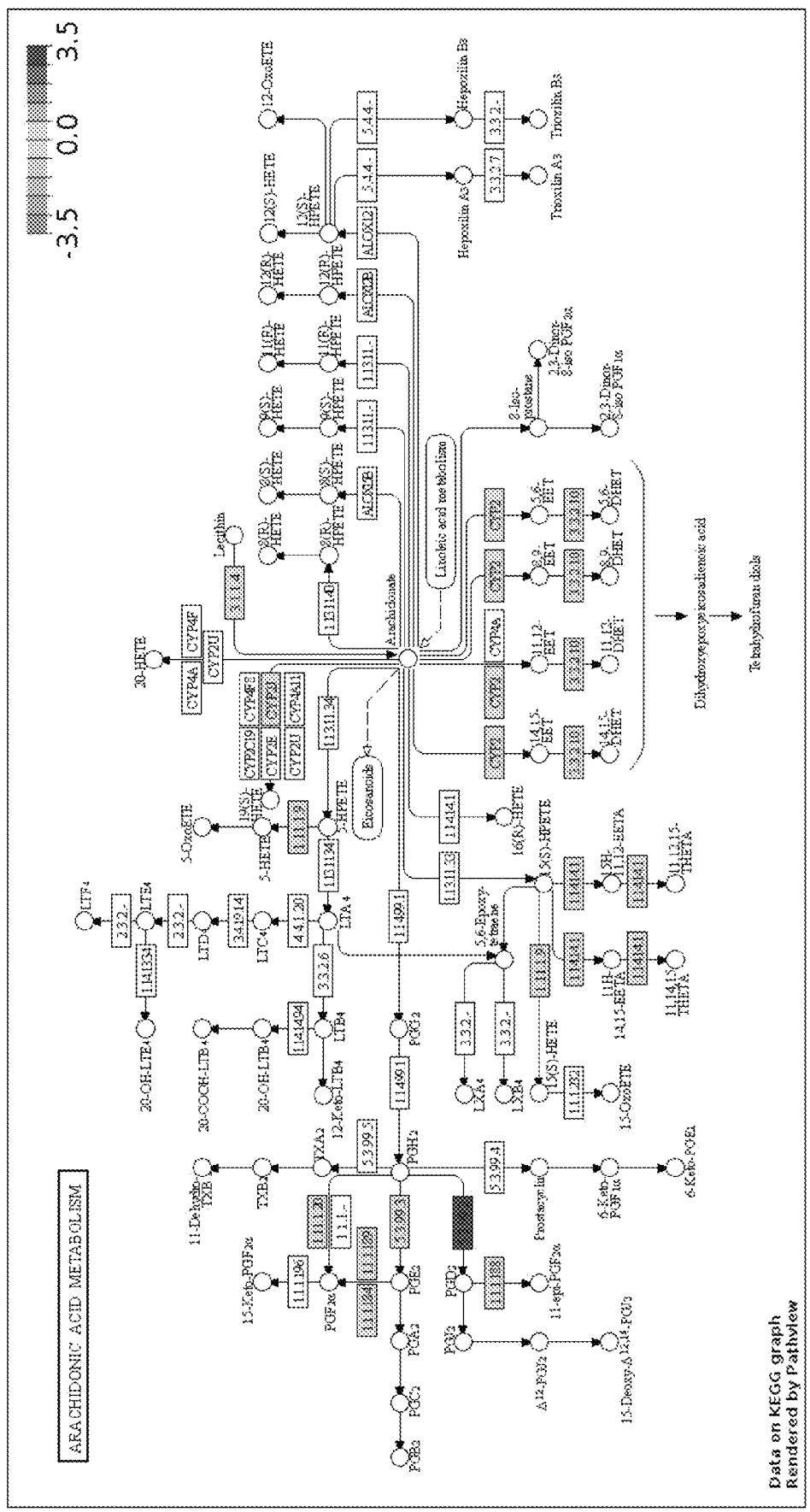

Overall results of single-cell transcriptome sequencing show that among obtained 21,884 genes, there are 16,537 genes with a value $p<0.05$ (FIG. 1A). Genes with an absolute value of a fold change between a cataract sample and a normal sample being larger than or equal to 1.5 times were screened: there were 36 genes with log 2 (FC)>1.5 and $p<0.05$, which indicated that up-regulated genes of the cataract sample relative to the transparent lens sample were expressed in red; and there were 16 genes with log 2 (FC)<−1.5 and $p<0.05$, which indicated that down-regulated genes of the cataract sample relative to the transparent lens sample were expressed in blue. Expressions of the PTGDS in the both samples were shown in a violin plot (FIG. 1B). Then, GSEA was performed on the 21884 genes through a KEGG database (FIG. 1C). It was found that a normative enrichment score (NES) of an arachidonic acid metabolism signaling pathway associated with the PTGDS was 1.52, and the value p was smaller than 0.05, suggesting that aging and opacity of a lens were closely related to this signaling pathway. Visualization of differential genes in the arachidonic acid metabolism signaling pathway was shown in FIG. 1D, and it was found that the PTGDS (5.3.99.2) played a role in catalyzing synthesis of the PGD2 in the arachidonic acid metabolism pathway. Through unsupervised cluster analysis, lens epithelial cells were divided into four subgroups (FIG. 2). The differential genes in various subgroups were screened according to $p<0.05$ and log 2 |FC|>1.5, and it was found that the PTGDS met the above screening criteria in each subgroup (FIG. 3). Expressions of the PTGDS in the aged opaque lens sample in various subgroups were all up-regulated compared with the transparent lens sample. Enrichment analysis was performed on genes of the two samples in various subgroups. Results of GSEA show that the arachidonic acid metabolism signaling pathways of the PTGDS in all the subgroups all had the value p smaller than 0.05 and |NES| larger than 1 (FIG. 4), suggesting that this pathway might play an important role in pathogenesis of aging and opacity of the lens. The differential genes of the arachidonic acid signaling metabolism pathway in each subgroup were visualized, and the PTGDS (5.3.99.2) could catalyze synthesis of PGD2. Therefore, it is proposed that the PTGDS may cause an oxidative stress injury of human lens epithelial cells by catalyzing synthesis of the PGD2, thereby promoting occurrence and development of aging and opacity of the lens (FIG. 5).

Embodiment 2

The PTGDS was expressed in both an age-related cataract sample and a transparent lens sample, and an expression level of a PTGDS gene in the former was significantly increased, as shown in FIG. 6A. The expression of the PTGDS in an HLEC-B3 cell line of a lens in vitro was confirmed by Western blot (FIG. 6B). AT-56 was added to the cell line. It was first found through an ELISA experiment on the PGD2 that 10 UM AT-56 more significantly inhibited production of the PGD2 compared with the AT-56 at other concentrations. Experimental results of CCK8 also further confirmed that the cell activities under the addition of the AT-56 with concentrations of 7 μM and 10 μM were higher than that with the addition of DMSO.

Figure 7:
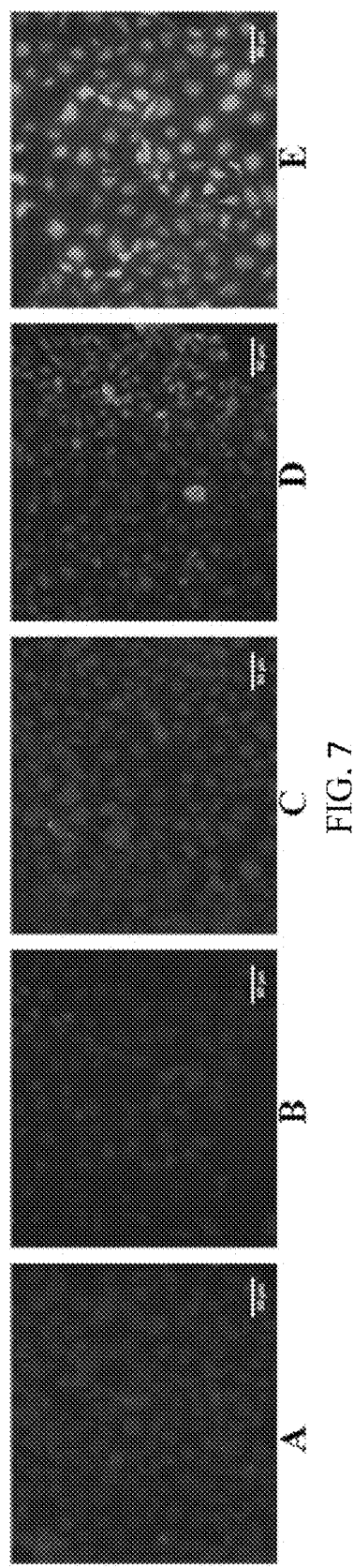
FIG. 7 is a diagram, in which A shows a control group (DMSO group); and B-E correspondingly show ROS fluorescence staining after the addition of PTGDS with concentrations of 100 pg/mL, 400 pg/mL, 700 pg/mL, and 1000 pg/mL, wherein a scale is as follows: A=B=C=D=E=50 μM.
Figure 8:
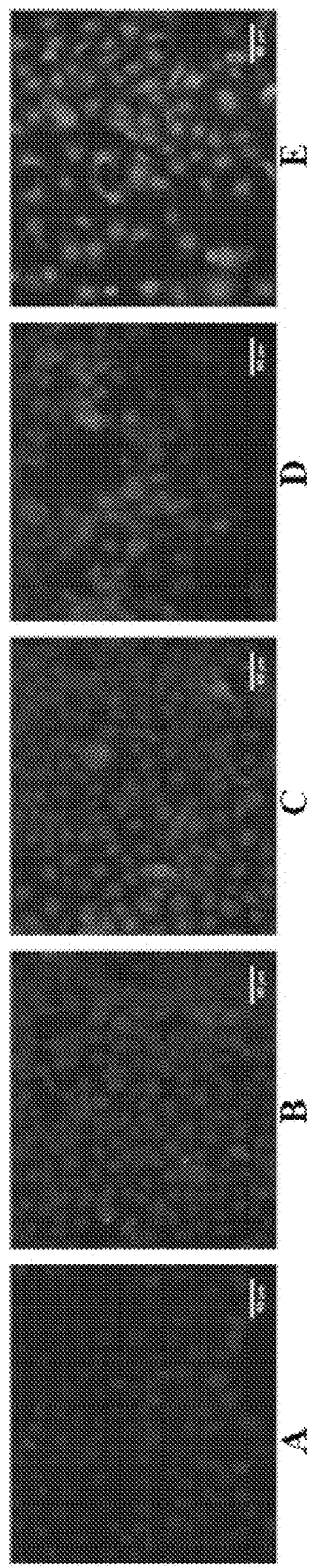
FIG. 8 is a diagram, in which A shows addition of DMSO; and B-E correspondingly show ROS fluorescence staining after the addition of PGD2 with concentrations of 0.1 nM, 0.4 nM, 0.7 nM, and 1.0 nML, wherein a scale is as follows: A=B=C=D=E=50 μM.
Figure 9:
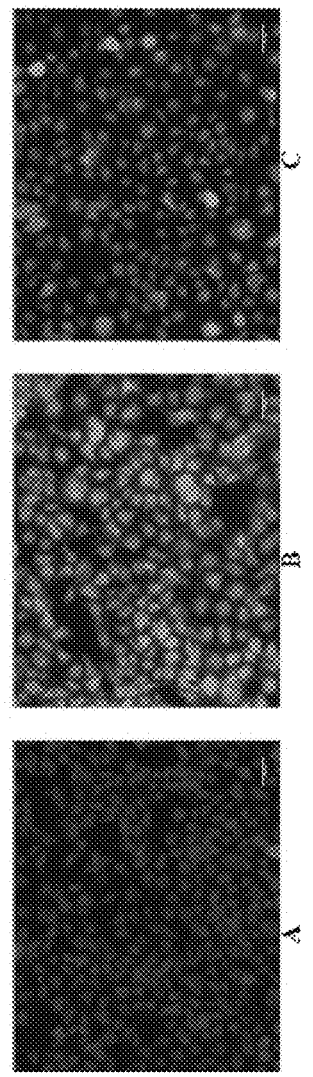
FIG. 9 is a diagram of AT-56 in an $H_2O_2$ epithelial cell oxidation model capable of inhibiting lens epithelial cells from producing ROS, wherein 9A shows a control group (DMSO group); 9B shows ROS fluorescence staining in an epithelial cell oxidation model with the addition of 200 μM $H_2O_2$; and 9C shows ROS fluorescence staining with the addition of 200 UM $H_2O_2$ and 10 μM AT-56, wherein ROS: green fluorescent staining, and a scale is as follows: A=B=C=100 μM.

The PTGDS and the PGD2 might both make levels of ROS produced by the lens epithelial cells increased, and were concentration-dependent. As shown in FIG. 7, A shows a control group (DMSO group); and B-E correspondingly show ROS fluorescence staining after the addition of PTGDS with concentrations of 100 pg/mL, 400 pg/mL, 700 pg/mL, and 1000 pg/mL, wherein a scale is as follows: A=B=C=D=E=50 μM; As shown in FIG. 8, A shows addition of DMSO; and B-E correspondingly show ROS fluorescence staining after the addition of PGD2 with concentrations of 0.1 nM, 0.4 nM, 0.7 nM, and 1.0 nML, wherein a scale is as follows: A=B=C=D=E=50 μM;

The AT-56 in an $H_2O_2$ epithelial cell oxidation model may inhibit lens epithelial cells from producing ROS (FIG. 9), wherein A shows a control group (DMSO group); B shows ROS fluorescence staining in an epithelial cell oxidation model with the addition of 200 μM $H_2O_2$; and C shows ROS fluorescence staining with the addition of 200 μM $H_2O_2$ and 10 UM AT-56, wherein ROS: green fluorescent staining, and a scale is as follows: A=B=C=100 μM.

Embodiment 3

PTGDS/PGD2 makes a content of MDA increased, and the AT-56 effectively reduces production of MDA.

Figure 10A:
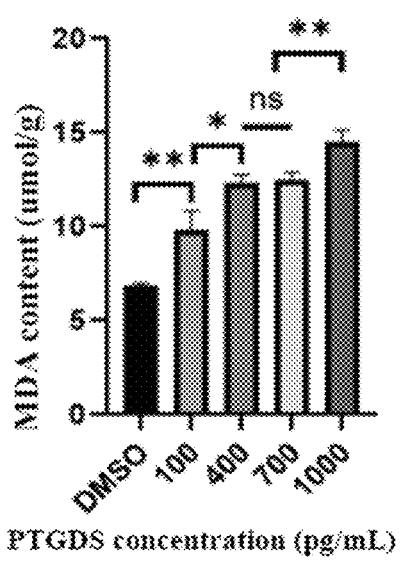
FIG. 10A shows contents of MDA at different concentrations of PTGDS.
Figure 10B:
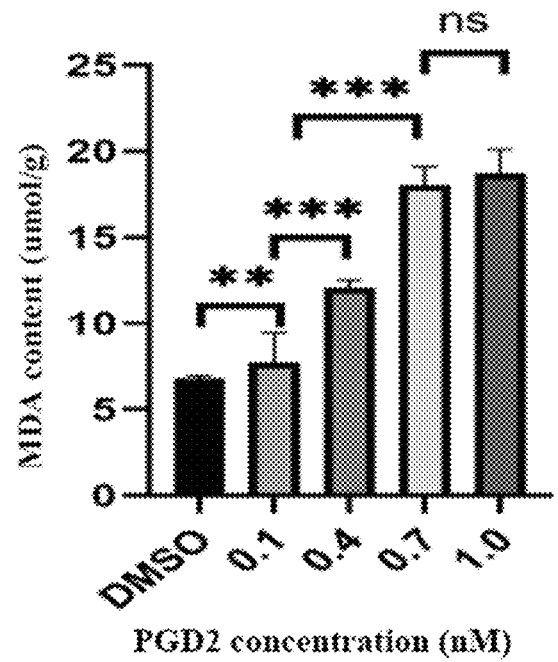
FIG. 10B shows contents of the MDA at different concentrations of PGD2.
Figure 10C:
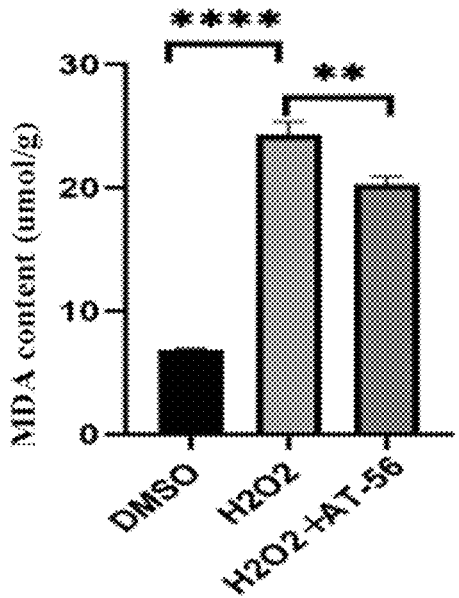
FIG. 10C shows a content of the MDA in a case of adding AT-56 to 200 μM $H_2O_2$.
Figure 11A:
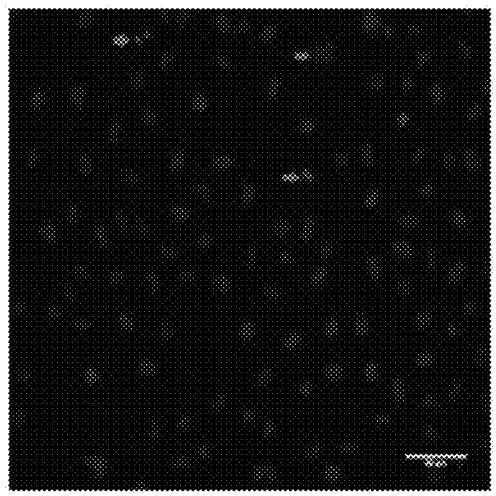
FIG. 11 is a diagram, in which A shows addition of DMSO; B shows addition of 200 μM $H_2O_2$; and C shows addition of 200 μM $H_2O_2$ and 10 μM AT-56, wherein red arrows represent apoptotic lens epithelial cells, and a scale is as follows: A=B=C=50 UM.
Figure 11B:
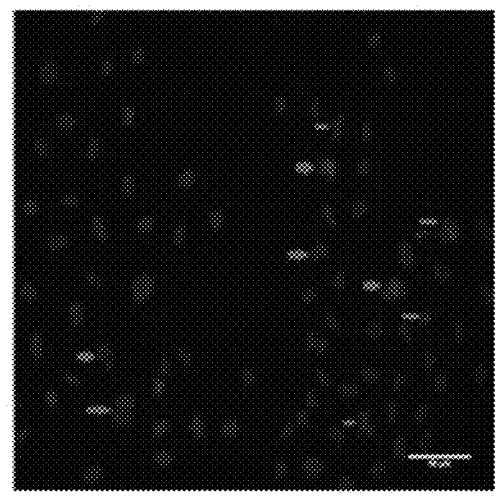
Figure 11C:
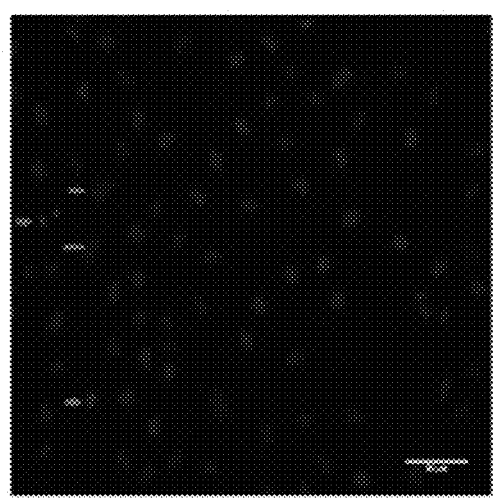
Figure 11D:
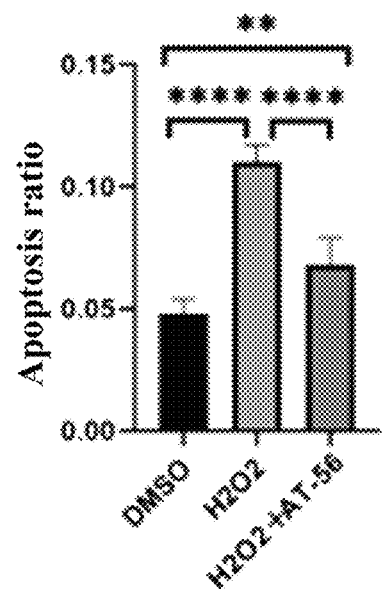
Figure 12:
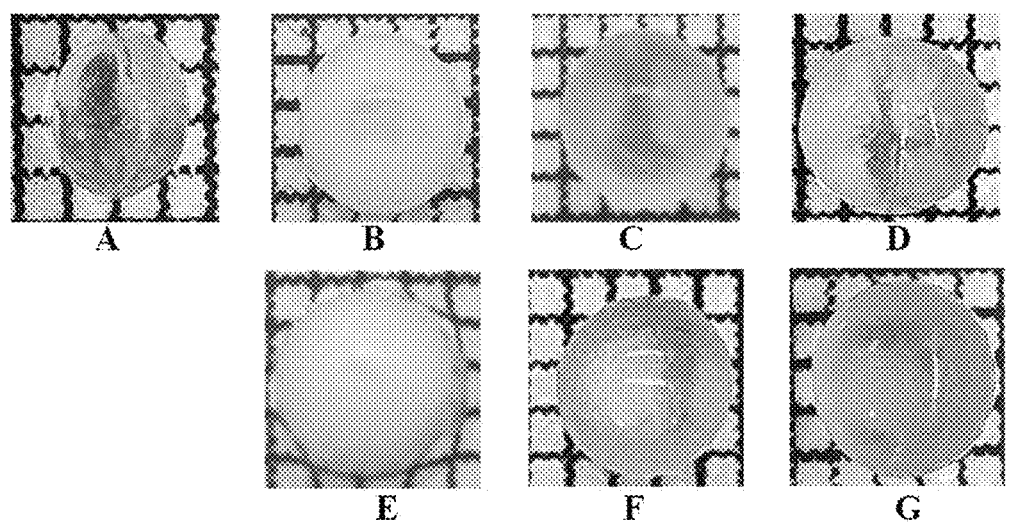
FIG. 12 is a diagram, in which A shows a blank control group; B shows treatment with addition of 200 μM $H_2O_2$ for 12 h; C shows treatment with 200 μm $H_2O_2$+7 UM AT-56 for 12 h; D shows treatment with 200 μm $H_2O_2$+10 μM AT-56 for 12 h; E shows treatment with addition of 200 μM $H_2O_2$ for 12 h; F shows treatment with 200 μm $H_2O_2$ for 12 h before treatment with addition of 7 μM AT-56 for 24 h; and G shows treatment with 200 μm $H_2O_2$ for 12 h before treatment with addition of 10 μM AT-56 for 24 h.

MDA is an important index of oxidative stress, and measurement on the content of the MDA reflects a degree of an oxidative stress injury. After addition of different concentrations of PTGDS (FIG. 10A) and PGD2 (FIG. 10B), values of MDA were measured. It was found that the content of MDA was increased with the increase of the concentration. The addition of AT-56 to $H_2O_2$ (FIG. 10C) might effectively reduce production of the MDA.

Embodiment 4

AT-56 reduces apoptosis caused by the oxidative stress injury.

If the lens epithelial cells suffer from the oxidative stress injury, excessive ROS may accumulate in the cells, which can cause apoptosis until generation of cataracts. As shown in FIG. 11, addition of 200 μM $H_2O_2$ to culture the lens epithelial cells results in apoptosis of more lens epithelial cells. In the other group, addition of 10 μM AT-56 to 200 μM $H_2O_2$ can effectively reduce apoptosis.

Embodiment 5

An in vitro oxidative opacity model for a rat lens verified that AT-56 could alleviate opacity, caused by $H_2O_2$ oxidative stress, of the lens.

From rat in vitro lens culture, it was found that the addition of AT-56 alleviated progression of the cataracts (FIGS. 12A-D). At the same time, after the cataracts were induced with $H_2O_2$, the addition of AT-56 could effectively reduce the degree of the cataracts (FIGS. 12E-G).

Notices for those skilled in the art: although the present invention has been described according to the above specific implementations, the invention idea of the present invention is not limited to the present invention, and any modification applying the idea of the present invention will be within the protection scope of the patent right of the present invention.

The invention claimed is:

1. A method for treating age-related cataracts comprising administering 7-10 UM of the prostaglandin D synthase (PTGDS) inhibitor 4-(5H-dibenzo[a,d]cyclohepten-5-ylidene)-1-[4-(2H-tetrazol-5-yl) butyl]-piperidine (AT-56).

2. A method for treating an oxidative stress injury of lens epithelial cells comprising administering 7-10 μM of the prostaglandin D synthase (PTGDS) inhibitor 4-(5H-dibenzo[a,d]cyclohepten-5-ylidene)-1-[4-(2H-tetrazol-5-yl)butyl]-piperidine (AT-56).

* * * * *